(12) United States Patent
Hashaikeh et al.

(10) Patent No.: US 9,446,000 B2
(45) Date of Patent: Sep. 20, 2016

(54) CELLULOSIC GEL MATERIAL AS A PHARMACEUTICAL EXCIPIENT

(75) Inventors: Raed Hashaikeh, Abu Dhabi (AE); Hatem M. N. Abushammala, Abu Dhabi (AE)

(73) Assignee: Masdar Institute of Science and Technology, Abu Dhabi (AE)

( * ) Notice: Subject to any disclaimer, the term of this patent is extended or adjusted under 35 U.S.C. 154(b) by 168 days.

(21) Appl. No.: 13/228,168

(22) Filed: Sep. 8, 2011

(65) Prior Publication Data

US 2013/0064892 A1  Mar. 14, 2013

(51) Int. Cl.

| | |
|---|---|
| *A61K 9/26* | (2006.01) |
| *A61K 9/20* | (2006.01) |
| *A61K 31/137* | (2006.01) |
| *A61K 31/167* | (2006.01) |
| *A61K 31/192* | (2006.01) |
| *A61K 31/343* | (2006.01) |
| *A61K 31/351* | (2006.01) |
| *A61K 31/381* | (2006.01) |
| *A61K 31/40* | (2006.01) |
| *A61K 31/41* | (2006.01) |
| *A61K 31/4184* | (2006.01) |
| *A61K 31/435* | (2006.01) |
| *A61K 31/4353* | (2006.01) |
| *A61K 31/4365* | (2006.01) |
| *A61K 31/4422* | (2006.01) |
| *A61K 31/4436* | (2006.01) |
| *A61K 31/445* | (2006.01) |
| *A61K 31/47* | (2006.01) |
| *A61K 31/497* | (2006.01) |
| *A61K 31/505* | (2006.01) |
| *A61K 31/519* | (2006.01) |
| *A61K 31/551* | (2006.01) |
| *A61K 31/554* | (2006.01) |
| *A61K 31/60* | (2006.01) |

(52) U.S. Cl.
CPC ........... *A61K 9/2054* (2013.01); *A61K 31/137* (2013.01); *A61K 31/167* (2013.01); *A61K 31/192* (2013.01); *A61K 31/343* (2013.01); *A61K 31/351* (2013.01); *A61K 31/381* (2013.01); *A61K 31/40* (2013.01); *A61K 31/41* (2013.01); *A61K 31/4184* (2013.01); *A61K 31/435* (2013.01); *A61K 31/4353* (2013.01); *A61K 31/4365* (2013.01); *A61K 31/445* (2013.01); *A61K 31/4422* (2013.01); *A61K 31/4436* (2013.01); *A61K 31/47* (2013.01); *A61K 31/497* (2013.01); *A61K 31/505* (2013.01); *A61K 31/519* (2013.01); *A61K 31/551* (2013.01); *A61K 31/554* (2013.01); *A61K 31/60* (2013.01)

(58) Field of Classification Search
CPC .... A61K 9/20; A61K 9/2004; A61K 9/2054; A61K 9/2059; A61K 9/2063; A61K 9/2095
USPC .................................................. 424/465–489
See application file for complete search history.

(56) References Cited

U.S. PATENT DOCUMENTS

| | | | |
|---|---|---|---|
| 7,951,400 B2 | 5/2011 | Desai et al. | |
| 7,977,473 B1 | 7/2011 | Lee | |
| 2001/0001658 A1* | 5/2001 | Chen | A61K 9/209 424/49 |
| 2003/0228368 A1* | 12/2003 | Wynn et al. | 424/486 |
| 2003/0232895 A1* | 12/2003 | Omidian | A61K 9/0065 521/99 |
| 2009/0117190 A1* | 5/2009 | Sato et al. | 424/486 |
| 2009/0170955 A1* | 7/2009 | Alur | A61K 9/2009 514/629 |
| 2010/0286387 A1 | 11/2010 | Hashaikeh et al. | |

OTHER PUBLICATIONS

Xiang et al (Heterogeneous aspects of Acid hydrolysis of α-Cellulose, Applied Biochemistry and Biotechnology, vol. 105-108, 2003).*
Xiang et al (Heterogeneous aspects of Acid hydrolysis of α-Cellulose, Applied Biochemistry and Biotechnology, vol. 105-108).*
Abushammala H and Hashaikeh R. Networked cellulosic gel material as a pharmaceutical excipient. Nanocon 2010, International Conference on Nanotechnology. Oct. 12-14, 2010, Olomouc, Czech Republic, EU, 5 pp.
Hashaikeh R and Abushammala H. Acid mediated networked cellulose: preparation and characterization. Carbohydrate Polymers. Jan. 30, 2011; 83(3): 1088-1094.
Abushammala HMN. Networked cellulose: preparation, characterization, and applications in pharmaceutical formulation and biofuel production. Thesis presented to the Masdar Institute of Science and Technology in partial fulfillment of the requirements for the degree of Master of Science in Materials Science and Engineering. Masdar Institute of Science and Technology. Jun. 1, 2011; pp. 1-82.
Rowe RC. The adhesion of film coatings to tablet surfaces—the effect of some direct compression excipients and lubricants. J. Pharm. Pharmac. 1977; 19: 723-736.
Pachulski N and Ulrich J. Production of tablet-like solid bodies without pressure by sol-gel processes. Letters in Drug Design & Discovery. 2007; 4: 78-81.
Abushammala H et al. Microcrystalline cellulose powder tableting via networked cellulose-based gel material. Powder Technology. Feb. 2012; 217; pp. 16-20.
International Search Report and Written Opinion, PCT/CA2012/000756, mailed Nov. 28, 2012.

* cited by examiner

*Primary Examiner* — Micah-Paul Young (74) *Attorney, Agent, or Firm* — Myers Bigel & Sibley, P.A.

(57) ABSTRACT

A method of making a pharmaceutical tablet comprises (a) combining (i) an aqueous networked cellulose gel with (ii) filler and (iii) an active agent to form a mixture thereof; (b) casting the mixture to form a wet tablet; (c) drying the wet tablet to form a dry pharmaceutical tablet; and then (d) optionally coating the tablet (e.g., with an enteric coating). Pharmaceutical tablets produced by such methods are also described.

22 Claims, 3 Drawing Sheets

Figure 1. Schematic representation of suggested network formation mechanism of acid mediated cellulose through re-crystallization

Figure 2. Schematic of the mechanism of encapsulation of MCC and active ingredient particles inside NC structure upon drying.

Figure 3. Hardness – NC concentration curve for the placebo tablets.

Figure 4. The tablet mold that was used to prepare the tablets.

Figure 5. Dissolution profile for Paracetamol tablets using 2% NC.

Figure 6. Full-release time for the Paracetamol tablets prepared using different NC concentrations.

US 9,446,000 B2

CELLULOSIC GEL MATERIAL AS A PHARMACEUTICAL EXCIPIENT

FIELD OF THE INVENTION

The present invention concerns pharmaceutical tablets and methods of making the same.

BACKGROUND OF THE INVENTION

Cellulose is a sustainable, renewable, environmentally-friendly, and biodegradable biopolymer that can be obtained from biomass and abundant resources. Cellulose has interesting properties and lends itself to modification; it has many derivatives and many modified forms. For many years, cellulosic polymers have been employed in the pharmaceutical industry.

Tablets are a major pharmaceutical dosage form. They are characterized by their hardness and ability for drug delivery. Tablets must be hard enough to tolerate any mechanical forces during packaging and transportation. At the same time, tablets hardness should be optimized to suit various drug delivery systems. Tablets are currently prepared by solid-state mixing of active ingredients with excipients such as starch, gelatin, and sugars. Wet or dry granulation is then performed to prepare the mixture for tablet compression using a punch machine [Edward M Rudnic, J. B. S., *Oral Solid Dosage Forms*. Remington: the science and practice of pharmacy. 21st ed. Philadelphia, Pa.: Lippincott Williams & Wilkins, 2005: p. 8921]. This technology is typically implemented by batch processing. Batch processing has many disadvantages including the variety of required equipments [Leuenberger, H., *New trends in the production of pharmaceutical granules: batch versus continuous processing*. European journal of pharmaceutics and biopharmaceutics, 2001. 52(3): p. 289-296] and batch-to-batch differences [E. M. Redunic, supra].

Continuous processing is promising technology that is used mainly in the food industry. Continuous processing is expected to be more economical and uses less equipment, labor and energy [A. Pellek, P. V. A., *Continuous Processing: Moving with or against the manufacturing flow*. Pharmaceutical Technology, 2008: p. 52-583]. Accordingly, there is a need for new ways to produce pharmaceutical tablets that are adaptable to continuous processing techniques.

SUMMARY OF THE INVENTION

We have prepared gel material from structure-modified or processed cellulose that has shown an interesting, high level of hardness compared to normal cellulose. This property can obviate the need for pressure in a tablet compression machine otherwise required to prepare hard tablets. Currently, to achieve the composition of tablets with acceptable good properties, complicated formulas are prepared and optimized after preparing and testing a large number of trial samples. Such procedures are time consuming and wasteful of materials and human resources. With the technology of the present invention, it was noted that hardness and drug delivery rate depend substantially on the percentage or ratio of the developed cellulosic gel material introduced in the formula. This relation allows controlling these properties by simply modifying the concentration of the cellulosic gel material in a suspension that is mixed with the active ingredient.

A first aspect of the present invention is a method of making a pharmaceutical tablet, comprising (a) combining (i) an aqueous networked cellulose gel with (ii) filler and (iii) an active agent to form a mixture thereof; (b) casting the mixture to form a wet tablet; (c) drying the wet tablet to form a dry pharmaceutical tablet; and then (d) optionally coating the tablet (e.g., with an enteric coating). The hardness of the pharmaceutical tablet is, advantageously, substantially determined by the ratio of networked cellulose to filler in said tablet, with a lower ratio providing a tablet of greater hardness.

A second aspect of the present invention is a pharmaceutical tablet comprising, consisting of, or consisting essentially of:
  (a) from 2 or 5 percent by weight to 60, 70 or 80 percent by weight of networked cellulose;
  (b) from 10 or 20 to 80, 90 or 95 percent by weight of filler;
  (c) from 0.1 or 1 to 10 or 20 percent by weight of an active agent; and
  (d) optionally, from 0.05 to 10 percent by weight of an enteric coating.

Examples of active agents that can be used to carry out the present invention include, but are not limited to, paracetamol (acetaminophen), aspirin, ibuprofen, naproxen, Atorvastatin, Clopidogrel, Esomeprazole, Amlodipine, Olanzapine, Valsartan, Risperidone, Venlafaxine, Pantoprazole, Montelukast, Quetiapine, Rosiglitazone, Pioglitazone, Simvastatin, Escitalopram, Donepezil, Irbesartan, Rosuvastatin, Aripiprazole, Candesartan, Sildenafil, Levofloxacin, Duloxetine, Methylphenidate, and pharmaceutically acceptable salts thereof (e.g., in an amount of from 0.01 or 0.1 to 200, 400, 2000 or 4000 milligrams per tablet).

The foregoing and other objects and aspects of the present invention are explained in greater detail in the drawings herein and the specification set forth below. The disclosures of all United States patent references cited herein are to be incorporated by reference herein in their entirety.

DETAILED DESCRIPTION OF THE PREFERRED EMBODIMENTS

"Active agent" as used herein may be any pharmaceutical active agent. The active agent is preferably water soluble, and is preferably a small organic compound such as an alkyl, heteroalkyl, aryl or heteroaryl compound, including derivatives thereof. The active agent may be provided in the form of a pharmaceutically acceptable salt thereof. Particular examples are given below "Filler" as used herein may be any suitable, preferably particulate, material. See, e.g., U.S. Pat. No. 7,771,744. Examples include, but are not limited to, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, anhydrous dicalcium phosphate, sodium starch glycolates, aluminosilicates, and combinations thereof (see, e.g., U.S. Pat. Nos. 7,771,744; 7,396,545; 7,374,779; and 7,208,176). In some embodiments, the filler comprises or consists essentially of a water insoluble material. In some embodiments, the filler comprises or consists essentially of microcrystalline cellulose.

"Cellulose" as used herein may comprise, consist of or consist essentially of any suitable natural cellulose material or partially processed cellulose, including but not limited to microcrystalline cellulose, hydroxymethyl cellulose, cellulose per se (e.g., cotton cellulose), hydroxypropyl cellulose, methylcellulose, and combinations thereof.

"Microcrystalline cellulose" is known. It is typically a purified, partially depolymerized cellulose that is prepared by treating alpha cellulose, in the form of a pulp manufactured from fibrous plant material, with mineral acids. See, e.g., U.S. Pat. No. 4,744,987. It is a generally white, odorless, tasteless, relatively free flowing powder that is generally insoluble in water, organic solvents, dilute alkalis and dilute acids. U.S. Pat. No. 2,978,446 to Battista et al. and U.S. Pat. No. 3,146,168 to Battista describe microcrystalline cellulose and its manufacture; the latter patent concerns microcrystalline cellulose for pharmaceutical applications.

"Dissolution media" as used herein may be any suitable dissolution media. In general, such a media breaks or disrupts the hydrogen bonding between individual cellulose chains and substantially isolates individual cellulose chains by surrounding them with ions and solvent molecules. Examples of dissolution media include, but are not limited to, acid solutions such as sulfuric acid, nitric acid, phosphoric acid, organic solvents, ionic liquids, basic solutions (e.g., NaOH, NaOH/Urea solutions) LiCl/DMAc solutions, and the like, including suitable combinations thereof.

"Antisolvent" as used herein may be any suitable antisolvent that coagulates the dissolved cellulose when mixed with the dissolution media. Examples include, but are not limited to, water, ethanol, methanol, acetone, and mixtures thereof.

Preparation of Gel and Combining with Filler and Active Agent.

The aqueous networked cellulose gel (sometimes also referred to as "coagulated cellulose", "hydrated cellulose gel" or "regenerated cellulose") used to carry out the present invention can be produced by any suitable technique. Examples of suitable aqueous networked cellulose gels and methods of preparing the same, include, but are not limited to, those disclosed in U.S. Pat. Nos. 7,790,457; 7,195,735; 6,875,756; 6,630,214; 6,630,214; 6,458,460; 6,391,376; 6,350,422; 6,344,189; 6,287,625; 6,350,422; 6,344,189; 6,315,907; 6,287,625; 6,096,258; 5,958,830; 5,932,270; 5,688,547; 5,498,420; 5,401,588; 5,306,685; 5,082,682; 4,341,807; 4,374,702; 4,378,381; 4,452,721; 4,452,722; 4,464,287; 4,483,743; 4,487,634; and 4,500,546.

In some embodiments, the gel is produced by, first, dissolving cellulose (including cellulose derivatives such as microcrystalline cellulose) in a dissolution media to form a first mixture. The first mixture is then combined with an antisolvent to form a precipitate. Once the precipitate is formed it can be separated from the antisolvent and dissolution media by any suitable technique (e.g., by centrifugation, filtering, settling, etc., including combinations thereof). Prior to and/or after separation, the pH of the precipitate can be adjusted (e.g., by dialysis and/or titration, optionally with mixing such as by sonication). In addition, the precipitate is preferably washed (prior to and/or after separation, and prior to and/or after pH adjusting) with an aqueous wash media (e.g., distilled water) to form the aqueous networked cellulose gel. The gel itself typically comprises, or consists essentially of, from 70, 80 or 90 percent to 99.5 or 99.9 percent by weight water; and from 0.1 or 0.5 to 10, 20 or 30 percent by weight networked cellulose. The aqueous networked cellulose gel typically has a pH of from 4, 5 or 6 to 7.5, 8 or 9.

After formation of the networked cellulose gel, the gel is combined with a filler (e.g., microcrystalline cellulose) and an active agent to form a mixture thereof. The ingredients can be combined or mixed by any suitable technique, such as stirring, inversion, sonication, agitation, etc. Once the ingredients are combined to form a substantially uniform mixture thereof, tablets can be formed from the mixture as discussed further below.

Tablet Forming, Drying and Further Processing

From the mixture described above, wet tablets are preferably formed by casting. Casting can be carried out in batch form or continuously by any suitable technique, such as by casting or slip casting. The casting is preferably carried out without the application of substantial external pressure, such as with a tablet press or mold, and can be carried out at ambient or atmospheric pressure (e.g., in a mold or form that is open to the atmosphere throughout the tablet formation and drying steps). The casting step may be carried out at ambient temperature or room temperature, at an elevated temperature, or at a reduced or chilled temperature (e.g., as in "freeze casting", N. Pachulski and J. Ulrich, A New Technique to Produce Pharmaceutical Tablet-Like Dosage Forms, pg 161 in BWIWIC 2006: $13^{th}$ International Workshop on Industrial Crystallization (Peter Jansens, Joop ter Horst, and Shanfeng Jiang Editors) The tablet may be formed in any suitable shape, including but not limited to spherical, ellipsoidal, and oblate spheroidal.

After casting, the tablets can be dried by any suitable technique, including but not limited to air drying at room temperature, by heating, by vacuum drying, or combination thereof. Preferably, the tablets shrink less than 20, 30 or 40 percent in diameter during said drying step. The dry tablets preferably do fracture under a force of 50 Newtons, or in some embodiments under a force 150 Newtons (e.g., as applied by opposing flat steel surfaces in a tablet press or tablet hardness tester, such as a Pharmatron or Dr. Schleuniger's tablet hardness tester). Advantageously, the hardness of the tablet is substantially determined by the ratio of networked cellulose to filler in that tablet, with a higher networked cellulose ratio providing a tablet of greater hardness.

The finished tablet will typically comprise, consist of, or consist essentially of:

(a) from 2 or 5 percent by weight to 60, 70 or 80 percent by weight of networked cellulose;

(b) from 10 or 20 to 80, 90 or 95 percent by weight of filler;

(c) from 0.1 or 1 to 10 or 20 percent by weight of an active agent; and (d) optionally, from 0.05 to 10 percent by weight of an enteric coating.

The tablet may be of any suitable total weight, for example, from 0.1 or 0.2 grams, up to 1, 2, 4 or 5 grams, or more (depending upon the size and species of the subject).

While in some embodiments the tablets preferably consist essentially of the foregoing ingredients, it will be appreciated that other pharmaceutical excipients and/or standard ingredients can optionally be included therein in relatively small amounts without departing from the invention. Examples of such other optional ingredients include, but are not limited to, anti-adherents, diluents, flavors, colors, lubricants, preservatives, sorbents, humectants, sweeteners, etc. (typically in a total amount of not more than 3, 5 or 7 percent by weight of the tablet).

While tablets of the invention are described primarily herein for human use, the tablets may also be prepared for veterinary purposes for administration to animals such as dogs, cats, cattle and horses for veterinary purposes.

As noted above, if desired the tablets may be coated with any suitable (typically polymeric) material, for example an enteric polymer (the term "enteric polymer" is a term of the art referring to a polymer which is preferentially soluble in the less acid environment of the intestine relative to the more acid environment of the stomach). See, e.g., U.S. Pat. No. 6,838,094.

An enteric coating may be an essentially conventional coating material, for example enteric polymers such as cellulose acetate phthalate, cellulose acetate succinate, methylcellulose phthalate, ethylhydroxycellulose phthalate, polyvinyl-acetatephthalate, polyvinylbutyrate acetate, vinyl acetate-maleic anhydride copolymer, styrene-maleic monoester copolymer, methyl acrylate-methacrylic acid copolymer, methacrylate-methacrylic acid-octyl acrylate copolymer, etc. These may be used either alone or in combination, or together with other polymers than those mentioned above. The enteric coating may also include insoluble substances which are neither decomposed nor solubilized in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin, 1,2-, 3,4-diepoxybutane, etc. The enteric coating may also include starch and/or dextrin.

Preferred coating materials are the pharmaceutically acceptable methacrylic acid copolymer which are copolymers, anionic in character, based on methacrylic acid and methyl methacrylate, for example having a ratio of free carboxyl groups: methyl-esterified carboxyl groups of 1:>3, e.g. around 1:1 or 1:2, and with a mean molecular weight of 135000.

Some of these polymers are known and sold as enteric polymers, for example having a solubility in aqueous media at pH 5.5 and above, such as the commercially available "Eudragit" (Trade Mark) enteric polymers, such as "Eudragit L 30" (Trade Mark) i.e. a cationic polymer synthesised from dimethylaminoethyl methacrylate, "Eudragit S" (Trade Mark) and "Eudragit NE" (Trade Mark).

Such polymers may be used either alone or with a plasticiser. Such coatings are normally applied using a liquid medium, and the nature of the plasticiser depends upon whether the medium is aqueous or non-aqueous. Aqueous plasticisers include propylene glycol or "Citroflex" or Citroflex A2" (Trade Marks) (mainly triethyl citrate or acetyl triethyl citrate). Non-aqueous plasticisers include these, and also diethyl and dibutyl phthalate and dibutyl sebacate.

The quantity of plasticiser included will be apparent to those skilled in the art. The enteric coating may also include an anti-tack agent such as talc, silica or glyceryl monostearate. The quantity of plasticiser and anti-tack agent may be generally conventional to the art. Typically the coating may include around 10-25 wt. % plasticiser and up to around 50 wt % of anti tack agent, e.g. 5-20 wt. % of anti-tack agent.

An enteric coating may be applied to the core by dissolving or suspending the enteric coating materials in a suitable medium, such as water, methanol, ethanol, isopropanol, acetone, methyl ethyl ketone, methylene chloride, ethylene chloride, ethyl acetate, etc. or mixtures thereof, and the resultant solution or suspension may be sprayed on the core to coat them, followed by drying sufficiently with an air flow and screening.

In the case of the preferred enteric coating material referred to above, the enteric coating material may be dissolved or suspended in a solvent for example water and coated onto the core using a fluidised bed system. If water is used, preferably an anti-foaming agent such as activated polymethylsiloxane is also included.

It may be desirable, particularly in the case of cores which contain highly soluble or moisture sensitive active materials, to first apply one or more sub-coats to the core, before application of the release retarding coating layer, the sub-coat consequently lying beneath the release retarding coating. Suitable sub-coat materials include hydroxypropylmethyl cellulose, for example of the known types E5 and E15 (Trade Marks) in mixture. It may also be desirable to apply one or more over-coats after application of the release retarding coating layer, the over-coat consequently lying over the release retarding coating. Suitable over-coat materials include copolymers of methacrylic acid and methyl methacrylate, and hydroxypropylmethyl cellulose. The over-coat may be of the same material as the sub-coat. Typically such coatings may be applied by known techniques of aqueous film coating.

Active Agents.

As noted above, any suitable active agent may be used to carry out the present invention. The active agents may be in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glutamine.

Particular examples of active agents, and preferred amounts thereof per tablet, include but are not limited to the following:

paracetamol (acetaminophen), preferably in an amount of from 1, 5, 10 or 100 milligrams per tablet, to 600, 1000 or 2000 milligrams per tablet;

aspirin, preferably in an amount of from 10, 20 or 40 milligrams per tablet to 400, 500 or 600 milligrams per tablet ibuprofen, preferably in an amount of from 5, 10, 100 or 200 milligrams per tablet, up to 2000 or 4000 milligrams per tablet;

naproxen (or naproxen sodium), preferably in an amount of from 500, 100 or 200 milligrams per tablet, up to 1000 or 1500 milligrams per tablet;

Atorvastatin (e.g., atorvastatin calcium), preferably in an amount of from 10 or 20 milligrams per tablet to 80, 100 or 150 milligrams per tablet;

Clopidogrel (e.g., clopidogrel hydrogen sulfate or clopidogrel bisulfate), preferably in an amount of 50 or 75 milligrams per tablet to 300, 400 or 600 milligrams per tablet;

Esomeprazole, preferably in an amount of from 1, 5, 10 or 20 milligrams per tablet to 40, 60 or 100 milligrams per tablet;

Amlodipine (e.g., amlodipine besylate), preferably in an amount of from 0.5 or 2.5 milligrams per tablet to 10, 20 or 50 milligrams per tablet;

Olanzapine, preferably in an amount of from 1 or 2.5 milligrams per tablet to 20, 40 or 50 milligrams per tablet;

Valsartan, preferably in an amount of from 5, 20, 40 or 80 milligrams per tablet to 320, 400 or 500 milligrams per tablet;

Risperidone, preferably in an amount of from 0.1 or 0.25 milligrams per tablet to 4 or 10 milligrams per tablet;

Venlafaxine (e.g., venlafaxine hydrochloride), preferably in an amount of from 1, 5, 10 or 25 milligrams per tablet to 100 or 200 milligrams per tablet;

Pantoprazole (e.g., pantoprazole sodium), preferably in an amount of from 1, 2, or 20 milligrams per tablet to 40 or 80 milligrams per tablet;

Montelukast (e.g., montelukast sodium), preferably in an amount of from 1 or 20 milligrams per tablet to 20, 30 or 40 milligrams per tablet;

Quetiapine (e.g., quetiapine fumarate), preferably in an amount of from 1, 5 or 10 milligrams per tablet to 20, 30 or 40 milligrams per tablet);

Rosiglitazone (e.g., Rosiglitazone maleate), preferably in an amount of from 1 or 2 milligrams per tablet to 10 or 20 milligrams per tablet;

Pioglitazone (e.g., pioglitazone hydrochloride), preferably in an amount of from 1, 5 or 10 milligrams per tablet to 50 or 60 milligrams per tablet);

Simvastatin, preferably in an amount of from 2 or 5 milligrams per tablet to 60, 80 or 100 milligrams per tablet;

Escitalopram, (e.g., escitalopram oxalate), preferably in an amount of from 1, 2 or 5 milligrams per tablet to 30, 40, 60 or 80 milligrams per tablet;

Donepezil (e.g., donepezil hydrochloride), preferably in an amount of from 1, 2 or 5 milligrams per tablet to 30, 40 or 50 milligrams per tablet;

Irbesartan, preferably in an amount of from 1, 5 or 10 milligrams per tablet to 300, 400 or 500 milligrams per tablet;

Rosuvastatin (e.g., rosuvastatin calcium), preferably in an amount of from 1, 2 or 5 milligrams per tablet to 40, 50 or 60 milligrams per tablet;

Aripiprazole, preferably in an amount of from 1 or 2 milligrams per tablet to 40, 50 or 100 milligrams per tablet;

Candesartan, preferably in an amount of from 1 or 2 milligrams per tablet to 40 or 50 milligrams per tablet;

Sildenafil (e.g., sildenafil citrate), preferably in an amount of from 1, 5, 10 or 20 milligrams per tablet to 100 or 200 milligrams per tablet);

Levofloxacin, preferably in an amount of 100, 200 or 300 milligrams per tablet to 600, 800 or 1000 milligrams per tablet;

Duloxetine (e.g., duloxetine hydrochloride), preferably in an amount of from 1, 2, 10 or 20 milligrams per tablet to 150 or 200 milligrams per tablet;

Methylphenidate (e.g., methylphenidate hydrochloride), preferably in an amount of from 1 or 2 milligrams per tablet to 80 or 100 milligrams per tablet.

The present invention is explained in greater detail in the following non-limiting Examples.

EXAMPLE 1

Formation of Networked Cellulose Gel

The process of acid dissolution and hydrolysis of cellulose depends mainly on its supramolecular structure that has crystalline areas and amorphous areas [E. Sjöström, *Wood chemistry: fundamentals and applications*: Academic Pr, 1993]. The selection of acid concentration is a key to the dissolution process. Previous work that investigated sulfuric acid hydrolysis of cellulose reported that acid concentrations below 64% would target the amorphous portion at an accelerated rate and the crystalline portion at a slower rate. This behavior of cellulose/64% acid mixture was utilized in isolating cellulose nanocrystals [J. F. Revol, et al., "Chiral nematic suspensions of cellulose crystallites; phase separation and magnetic field orientation," *Liquid Crystals*, vol. 16, pp. 127-134, 1994; X. M. Dong, et al., "Effect of microcrystallite preparation conditions on the formation of colloid crystals of cellulose," *Cellulose*, vol. 5, pp. 19-32, 1998]. Working at higher concentrations would disrupt the crystalline structure and dissolve cellulose chains. As a result, the whole cellulose material becomes equally exposed to hydrolysis. There is a short window between the process of disruption of the crystalline structure and the process of hydrolysis. This process has controlled parameters which are mainly acid concentration, mixing time and temperature. This study focused on developing optimized parameters with the target of getting cellulose chains into solution while minimizing degradation and cleavage of the glycosidic bond. These chains will then be precipitated in a different form using anti-solvent such as water or ethanol. The parameters were optimized to achieve dissolution, avoid degradation and maximize yield of precipitated material. Dried films of the generated material were characterized to identify applicable properties.

The production conditions for NC were optimized so that it was produced in a high yield in addition to a high hardness value. NC was prepared by acid dissolution of MCC and regeneration in ethanol. The dissolution temperature and time were varied while acid concentration was kept constant at 70%. The resultant suspensions were dried then studied using X-ray diffraction, transmission electron microscopy, thermogravemetric analysis, and nanoindentation. NC was also prepared using cotton cellulose and using ionic liquids as a solvent instead of sulfuric acid.

Methodology

Materials.

Microcrystalline cellulose was provided by FMC BioPolymer (Avicel-PH101). Filter paper purchased from Whatman® was grinded and used as source of cotton cellulose. Sulfuric acid, 95-97%, Reagent Grade, was purchased from Scharlau. Ethanol, Dimethylacetamide, Lithium chloride and 1-Ethyl-3-methylimidazolium acetate were purchased from Sigma-Aldrich.

NC Suspension Preparation Using Sulfuric Acid.

Microcrystalline cellulose powder was mixed with 70% (w/w) $H_2SO_4$ at a ratio of 1 g cellulose/10 ml $H_2SO_4$ using Varian Dissolution System (VK7010) at different temperatures and for different times with 250 rpm agitation. After mixing, a white material was precipitated by adding either ethanol (−17° C.) or water (4° C.) as anti-solvents. The volume of anti-solvent used was equivalent to the volume of acid used. The product was collected and washed with DI water through centrifugation three times at 4700 rpm for 10 minutes using Allegra™ 25R Centrifuge. Centrifugation was conducted at 4° C. The centrifugation process resulted in separating the precipitated cellulose material from the spent liquor. The precipitate was collected again and dialyzed for three days until the pH is 6-7. The resultant white suspension was weighed then sonicated using Hieschler Ultrasonic Processor UP400S for 30 minutes. Portion of the sonicated suspension was freeze-dried using VirTis Wizard 2.0 Freeze Drier. After dialysis the yield was calculated by withdrawing a known amount of small sample and obtaining its oven-dried weight. The yield is calculated based on the solid product weight after hydrolysis and drying compared to the starting weight.

Microstructure Analysis.

X-ray diffractograms of the oven dried samples were obtained on an X-ray diffractometer (PANalytical, X'Pert Pro). Microstructure images were obtained using JEOL 2011 High Contrast Digital Transmission Electron Microscopy (TEM). Samples were prepared by air drying the cellulose suspension on Quantifoil® grids (SPI).

Hardness Using Nanoindentation.

About 25 ml of the resulting sample was taken in a small beaker and subjected to air drying in a shaker (80° C.) for few hours (~4 hours) till a dry thick film was formed. The dry film was used for making samples for nanoindentation. Nanoindentation measurements were carried out at room temperature with an MFP 3D Asylum Research Nanoindenter in an acoustic box. The indenter was a cube corner tip with a spring constant of 3.78 µN/nm.

Hardness Using Tablet Hardness Tester.

Tablets were prepared by casting the suspension and leaving it to air-dry for one day. The hardness of the resultant tablets was measured using a Dr. Schleunger® Pharmaton 8M Tablet Tester.

Thermogravemetric Analysis

Thermal characteristics of NC material were investigated by using thermogravimetric analyzer (TGA). The sample, 6-10 mg, was analyzed by increasing the temperature at a rate of 10° C./min in a stream of nitrogen (20 ml/min).

Degree of Polymerization Using Gel Permeation Chromatography.

Mobile Phase Preparation.

10 g of lithium chloride salt (LiCl) was transferred to 1000 mL of dimethylacetamide (DMAC) and stirred for two hours. The solution was filtered by vacuum through 0.45 µm FHLP Millipore® membrane filter.

Sample Preparation.

100 mg of cellulose was transferred to a 100 mL volumetric flask containing 10 mL of 10% LiCl/DMAC solution. The sample was heated at 120° C. and stirred for 12 hours. Then it was diluted to volume using 1% LiCl/DMAC solution.

Chromatographic Conditions.

Using Viscotek® GPCmax VE2001 (gel permeation chromatography) with TDA305 (triple detection array), 100 µL of the sample was injected to a ViscoGEL™ column, which was kept at a temperature of 35° C. Light scattering detector (LSD), refractive index detector (RID), and viscosity detector (IVD) were used for detection using refractive index increment (dn/dc) of 0.134. 32

NC Suspension Preparation Using Ionic Liquids.

Microcrystalline Cellulose powder was mixed with 1-ethyl-3-methylimidazolium acetate at a ratio of 1 g cellulose/20 ml ionic liquid using Varian Dissolution System (VK7010) at ambient temperature for 30 minutes with 250 rpm agitation. After mixing, a white material was precipitated by adding ethanol. The volume of ethanol used was equivalent to the volume of 1-ethyl-3-methylimidazolium acetate used. The product was collected and washed with DI water through centrifugation three times at 4700 rpm for 10 minutes using Allegra™ 25R Centrifuge. The centrifugation process resulted in separating the precipitated cellulose material from the spent liquor. The precipitate was collected and weighed then sonicated using Hieschler Ultrasonic Processor UP400S for 30 minutes. Portion of the sonicated suspension was freeze-dried using VirTis Wizard 2.0 Freeze Drier. The yield was calculated by withdrawing a known amount of small sample and obtaining its oven-dried weight. The yield is calculated based on the solid product weight after dissolution and drying compared to the starting weight.

Results and Discussion

Acid Dissolution and Structural Changes.

The intention here is to study the preparation of NC by dissolution of MCC using sulfuric acid. It is well reported [Q. Xiang, et al., "Heterogeneous aspects of acid hydrolysis of -cellulose," *Applied biochemistry and biotechnology*, vol. 107, pp. 505-514, 2003; P. H. Hermans and A. Weidinger, "Recrystallization of amorphous cellulose," *Journal of the American Chemical Society*, vol. 68, pp. 1138-1138, 1946] that dissolved cellulose favors regeneration into the more thermodynamically stable cellulose II microstructure. In this work, we used the formation of cellulose II as an indication for dissolution and the yield as an indication to the degree of hydrolysis. In the first set of experiments the effects of acid concentration and the capability of the chosen concentration of 70% to dissolve cellulose were studied (the 70% acid concentration was chosen based on a preliminary work that is not reported here). X-ray diffraction data of the treated, washed, dialyzed and dried material (not shown) were examined. The data give an indication of the dissolution behavior of cellulose by clearly showing the phase change from cellulose I to cellulose II. Acid concentration of 70% was able to completely dissolve cellulose.

The X-ray diffraction pattern of MCC is a typical pattern of crystalline cellulose I. The X-ray diffraction pattern of the regenerated material shows mainly amorphous cellulose with weak peaks characteristic of cellulose II. The treatment process modified cellulose crystallinity. Cellulose was regenerated into a new, less ordered structure. A significant portion of the regenerated material is amorphous. We assume that re-crystallization occurs within the suspension at the moment of introducing the anti-solvent. Since cellulose II peaks intensity in the oven dried samples are stronger than those for the freeze dried ones, there is the possibility of cellulose II structure formation upon drying as well. It could also be possible that the freeze drying process disrupts the order in the sample and reduce its crystallinity.

High Yield Production.

According to Table 1, a range of NC suspensions were prepared under different conditions. The data in Table 1 suggest that temperature is the main factor that affects the yield. Using conditions of NC5, high yield values of 97.4% were obtained at low temperature (5° C.). Other factors such as time and anti-solvent (water or ethanol) can affect the yield as well, especially at low temperature.

TABLE 1

Dissolution conditions for the preparation of a variety of NC suspensions. The yield is mainly controlled by temperature. Low temperatures decrease the kinetics of acid hydrolysis and increase the process yield.

| Run | Temperature (° C.) | Time (min) | Precipitating Agent | Yield (%) |
|---|---|---|---|---|
| NC1 | 35 | 20 | Water | 11.8 |
| NC2 | 25 | 10 | Water | 47.6 |
| NC3 | 25 | 10 | Ethanol | 51.4 |
| NC4 | 5 | 60 | Ethanol | 60.6 |
| NC5 | 5 | 30 | Ethanol | 97.4 |
| NC6 | 5 | 30 | Water | 72.7 |

The results revealed that high yield values can be achieved at low temperature and short time with ethanol as a precipitating agent. We have used ethanol as a precipitating agent for two main reasons. First, it can be efficient in stopping the hydrolysis reaction by quenching and dilution. Ethanol can be cooled to low temperatures below its freezing point (−114° C.). In our work we used ethanol at regular freezers temperature of (−17° C.). The second reason for using ethanol is that future process development for mass production of acid treated cellulose will benefit from the use of ethanol as anti-solvent. Ethanol is a light material which can be easily separated from the concentrated acid upon treatment with cellulose.

There are several available technologies for low cost-efficient separation of ethanol from concentrated sulfuric acid. The challenge would be to perform this separation process in an energy efficient manner focusing on recovering the initial acid concentration to be recycled for cellulose treatment. One example technique for efficient separation is by using humidified air saturated with ethanol at 40° C. to strip out the ethanol from the acid mixture [G. E. Lightner, "Method to separate ethanol from a solution containing sulfuric acid and ethanol," U.S. Pat. No. 6,432,276].

Using the conditions of NC5 is the most efficient for the production of NC suspension because of the high yield that can be obtained by these conditions. Five replicate experiments were conducted at the same conditions as NC5 and all gave an average yield of 97.1% (Standard Deviation (SD) =0.22). The temperature and the time were optimum for the cellulose to modify and form special arrangement of its hydrolyzed chains that can be precipitated in high yield. We can also notice that despite of the identical conditions for NC5 and NC6, the yield is different. It is expected to have low yield from NC6 since water is not good as a precipitating agent. Some of the material were lost because it stayed soluble in water and then washed out (not shown).

Tablet Hardness and Nanoindentation.

The hardness of the resultant NC material was measured in two different ways; using tablet hardness tester and using nanoindentation. Tablets were prepared by simple casting of the suspensions and tested using Dr. Schleunger® Pharmaton 8M Tablet Tester. All the suspensions' tablets needed more than the maximum limit of the instrument, i.e. 450 N, to disintegrate. This is a high hardness value of a cellulosic material.

For measuring the hardness via nanoindentation, oven-dried samples of all suspensions were indented to a displacement of 400 nm with displacement velocity of 40 nm/s. The hardness and the elastic modulus were calculated after analyzing the resultant force-displacement curves by Oliver-Pharr model. Force-displacement curves were obtained by multiple indentations to 400 nm for one of the oven-dried NC suspensions (not shown). The elastic modulus and hardness values are given in Table 2. The results of the mechanical properties of NC material support the fact that NC5 conditions are optimum. The conditions of NC5 produced hard material with an elastic modulus of 9.9 GPa.

TABLE 2

Mechanical properties of the NC materials measured via nanoindentation. The conditions of NC5 produced hard material.

| Run | Temperature (° C.) | Time (min) | Precipitating Agent | Hardness (Pa) | Modulus (GPa) |
|---|---|---|---|---|---|
| NC3 | 25 | 10 | Ethanol | 299 | 3.3 |
| NC4 | 5 | 60 | Ethanol | 351 | 3.3 |
| NC5 | 5 | 30 | Ethanol | 801 | 9.9 |
| NC6 | 5 | 30 | Water | 468 | 7.2 |
| MCC | — | — | — | 434 | 4.2 |

Shrinkability.

The new material seems to gain significant hardness compared to starting MCC. In order to understand the reason behind this significant increase in hardness, it is worth mentioning here that, when dried, the sample shrinks significantly in volume. The sudden precipitation using the anti-solvent caused cellulose chains to connect in different ways to form a three dimensional network. The formation of this network changes the cellulose crystallinity, microstructure, morphology and as a result its properties. Shrinkability is an indication of the network nature of the material. When dried to gel form, and upon further drying, the prepared suspension shrinks while maintaining its integrity (not shown).

Microstructure Imaging.

The nanostructure of NC was imaged using TEM (not shown). The images reveal a network structure. The images suggest that chains bundle together randomly. This indicates that during the regeneration process of cellulose from solution, the chains are bonded to neighboring chain when the acid solvent is withdrawn (diluted) by the addition of ethanol. However, due to the randomness and the quick precipitation, the joining of chains is limited to short lengths. Networking occurs when chains are split to join different bundles.

Thermal Degradation.

Thermal stability of the different NC freeze-dried samples was studied using thermogravimetric analysis. The TG and DTG curves of freeze-dried sample of NC were compared with MCC (not shown). The DTG peak for MCC degradation is centered at 350° C. The degradation behavior of the NC material was different and showed lower degradation temperature. The onset degradation temperature for NC was 225° C. and a wide peak centered at 325° C. The drop in the weight is mainly caused by the degradation of the cellulose chains and the evolution of non-combustible gases (carbon dioxide, carbon monoxide, formic acid, and acetic acid). In addition, pyrolysis and evolution of combustible gases occur [S. L. LeVan, "In A P Schniewind (Ed.) Concise encyclopedia of wood & wood-based material pp. 271-273," ed: Elmsford, N.Y.: Pergamon Press, 1989.]. It is also observed that NC material exhibits a small peak at about 50° C. due to the evaporation of adsorbed water. The amount of adsorbed water is related to the amorphous nature of NC material.

Previous study by Roman et al. [M. Roman and W. T. Winter, "Effect of sulfate groups from sulfuric acid hydrolysis on the thermal degradation behavior of bacterial cellulose," *Biomacromolecules*, vol. 5, pp. 1671-1677, 2004] on the thermal degradation of sulfuric acid hydrolyzed material suggested that sulfating is the reason the observed thermal behavior of low degradation temperatures. We tend, however, to believe that the decrease in thermal stability of the acid treated material is due to the increase in amorphous content. The increase in amorphous material content in the sample is evidenced from XRD data and the water desorption peaks at 50° C. Cellulose has an amazing capability of catching and holding on to water which is bound by hydrogen bonding. At the same time, water cannot penetrate cellulose if it is crystalline [M. Muller, et al., "All disordered regions of native cellulose show common low-frequency dynamics," *Macromolecules*, vol. 33, pp. 1834-1840, 2000]. The increased capacity of the treated samples to hold into water is a clear indication of increased amorphous portion.

Network Formation Mechanism.

Figure 1:
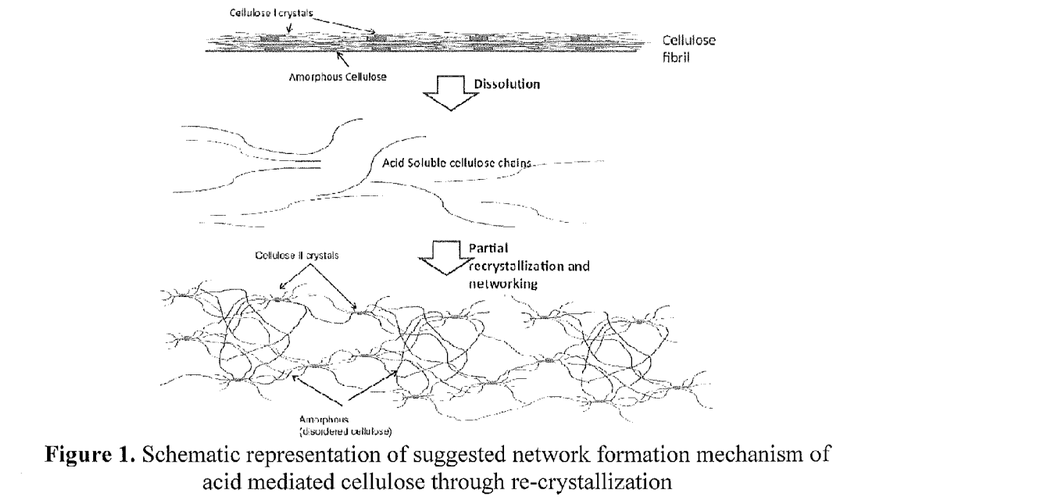
FIG. 1. Schematic representation of network formation mechanism of acid mediated cellulose through re-crystallization. Due to the substantial randomness that occurs through mixing, bundling and re-crystallization occur in a substantially random, three dimensional, way.

The schematic in FIG. 1 summarizes the proposed acid dissolution mechanism and possible pathway toward network formation. Due to the crystalline nature of cellulose where individual crystals consist of layers of cellulose chains bound to each other by hydrogen bonding, the concentrated acid starts by opening up this structure. When treating cellulose with concentrated sulfuric acid, dissolution occurs by disrupting the hydrogen bonds linking two chains together. Individual cellulose chains become soluble in the acid. The extent of hydrolysis (breakdown) of the acid-soluble cellulose chains will then depend on the reaction time at the given 70% acid concentration and temperature. The low temperature of 5° C. seems to be good enough to slow the hydrolysis reaction. Adding anti-solvent in which cellulose is not soluble while sulfuric acid is soluble will withdraw the acid from between cellulose chains and results in cellulose chains touching, bundling and re-crystallizing into the more stable cellulose II. Due to the randomness that occurs through mixing, bundling and re-crystallization occur in a random three dimensional way. Significant portion of the chains do not have the conditions to re-crystallize and as a result the percentage of re-crystallization is low and is distributed throughout the sample. This is confirmed by XRD data where the bulk of the sample is amorphous with weak crystalline peaks.

Preparation of NC by Regeneration of MCC in Ionic Liquids.

MCC was dissolved in 1-ethyl-2-methylimidazoliume acetate and regenerated in ethanol. Ionic liquids are promising due to their uncorrosive and green properties compared to sulfuric acid. Also ionic liquids only dissolve cellulose without hydrolyzing it. Hence, 100% yield is achievable (99.6%). The XRD diffractogram for freeze-dried sample of NC prepared using ionic liquids was similar to the diffraction pattern of freeze-dried NC that was previously prepared using sulfuric acid (not shown). The similar diffraction patterns and the close yield values are an indication that sulfuric acid at the optimum conditions worked only as a solvent, i.e. it did not hydrolyze MCC.

Preparation of NC by Regeneration of Cotton Cellulose in Sulfuric Acid and Ionic Liquids Cotton cellulose (CC) was used as another source of cellulose. It has different properties compared to MCC such as crystallinity and degree of polymerization. CC has high degree of polymerization compared to MCC. The degree of polymerization of MCC and CC was measured using Viscotek® GPCmax VE2001 (gel permeation chromatography) with TDA305 (triple detection array). The degree of polymerization of MCC is 240 while it is 777 for CC.

The XRD pattern (not shown) indicated that NC can also be prepared using other source of cellulose with different properties. The NC yields were 94.5% and 99.2% using sulfuric acid and ionic liquids, respectively. The different properties of CC may affect the properties of the NC material.

Conclusion.

High-yield networked cellulose was prepared by dissolution of cellulose followed by regeneration in ethanol. The NC structure is networked and has mainly an amorphous phase with a crystalline portion characteristic of cellulose II. The material showed significant shrinkability upon drying, improved hardness, and increased structure accessibility. The gel material was prepared using different cellulose resources such as microcrystalline cellulose and cotton cellulose and using different solvents such as sulfuric acid and ionic liquids.

EXAMPLE 2

Production of Pharmaceutical Tablets

Two main properties of networked cellulose were observed and/or measured. These properties are the high mechanical stability and shrinkability. These properties are a result of the networked structure of the NC material and the reason behind studying this material as a multifunctional tablet excipient. The porosity can provide the space for the active molecules to occupy. The active ingredient particles are loaded inside a wet NC matrix; it is slip-casted and left to dry. Upon drying, the formula shrinks in volume and entraps the particles. After administration the tablet can swell and release the active particle when exposed to aqueous medium. So NC works as binder and disintegrant and can be accompanied with untreated cellulose as diluent.

Other importance of the utilization of NC in pharmaceutical formulation is the significant impact it has on the manufacturing process itself. The gel nature of NC eases the production process and improves the quality of the finished product. The achieved simplicity of tablet production allows implementing continuous processing.

Methodology

Materials.

Microcrystalline cellulose (MCC) was provided by FMC BioPolymer (Avicel-PH 101). Filter paper purchased from Whatman® was grinded and used as source of cotton cellulose. Sulfuric acid, 95-97%, Reagent Grade, was purchased from Scharlau. Ethanol and Paracetamol (Acetaminophen) were purchased from Sigma-Aldrich. Sulfuric acid, 95-97%, Reagent Grade, was purchased from Scharlau. Ethanol and 1-Ethyl-3-methylimidazolium acetate were purchased from Sigma-Aldrich.

NC Material Preparation Using Sulfuric Acid.

Details of the preparation of NC material have been covered in Example 1 above. NC was prepared via sulfuric acid dissolution of MCC. NC suspensions, with different concentrations, were prepared either by drying or diluting to a given weight.

Placebo Tablets Preparation.

Placebo tablets were prepared by mixing 75 g of each of the previously prepared NC suspensions with 15 g of MCC. The formulas were slip-casted and left to air-dry for one day. The concentrations of the used NC suspensions were 2.00%, 4.72%, 6.25%, 8.02%, 9.20%, and 11.66%.

Paracetamol Tablets Preparation.

Paracetamol tablets were prepared by mixing 75 g of NC suspension with 12.6 g of MCC and 2.4 g of Paracetamol. The formulas were slip-casted and left to air-dry for one day. The tablets were prepared in order to have a label claim of 30 mg Paracetamol. Five NC concentrations were used; 2%, 3%, 4%, 5%, and 6% in order to study the effect of NC concentration on the properties of the finished product.

Placebo and Paracetamol Tablets Testing.

The hardness of the slip-casted tablets was measured using Dr. Schleunger®Pharmaton 8M tablet hardness tester. The friability test was conducted using Erweka® TA220. For mass variation, twenty tablets were weighed individually. The relative standard deviation was calculated. All tests were conducted as per XXIV monograph in the United State Pharmacopeia (USP) for uncoated tablets.

To measure the content uniformity of the Paracetamol tablets, they were powdered then 30 mg equivalent weight of Paracetamol was transferred into a 250 mL volumetric flask. 200 mL of water was added to the flask and sonicated for 5 minutes then completed up to volume with water (sample stock solution). 10 mL of the stock solution was transferred into a 50 mL volumetric flask and completed up to volume by water. A portion of the solution was filtered using 0.2 μm PTFE filter. The absorbance of the filtrate was measured using Thermo Evolution300 UV spectrophotometer at 243 nm with a cell path of 10 mm. The Paracetamol content was measured against standard with the same final concentration (0.024 mg/mL). The test was repeated for 10 tablets. The average and relative standard deviation were calculated.

Paracetamol release was studied using Varian VK7010 Dissolution system connected to Cary50 UV spectrophotometer by fiber optics cords. The release was measured for six tablets, each in 900 mL of water at 37.0° C. using paddle agitation of 50 rpm. The absorbance of the medium was directly measured from the vessel at different time intervals at 243 nm using cell path of 10 mm. The percentage Paracetamol release was measured against Paracetamol standard with a concentration of 0.033 mg/mL.

Results and Discussion

MCC Hydrolysis and Structure Modification.

Figure 2:
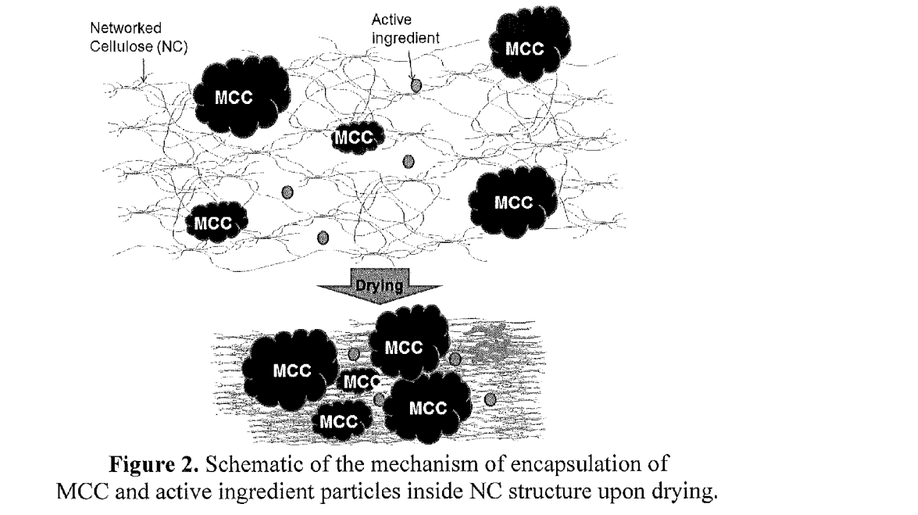
FIG. 2. Schematic of the mechanism of encapsulation of microcrystalline cellulose (MCC) and active ingredient particles inside networked cellulose (NC) structure upon drying. NC is mixed with MCC and active ingredient molecules. Upon drying, it shrinks in volume entrapping them inside its structure.

The gel form of networked cellulose has high porosity structure. This can provide enough space to be occupied by additives such as molecules of active ingredients. At the same time, NC material has enhanced shrinkability and swelling as a result of the increase in the amorphous content. MCC particles were used to provide structural integrity and reduce shrinkability effects. The active ingredient and MCC particles are loaded inside a wet NC matrix; it is slip-casted and left to dry. Upon drying, the formula shrinks in volume and entraps both the active ingredient and the MCC particles. FIG. 2 shows a schematic of the mechanism by which NC encapsulates MCC and active ingredient particles.

Both MCC and NC are of the same material, but with different structures. As a result, the bonding between the two is likely to occur because of hydrogen bonding and entanglement of the MCC within the network. Due to the preparation technique of NC material, where networked fibers are produced in an aqueous suspension, the NC is present in expanded form to cover large space that is filled with water. Mixing of MCC and active ingredients at this status allows excellent distribution of all components.

Cellulose chains have intermolecular forces such as hydrogen bonding and van der Waals forces between them which favor the alignment and aggregation of cellulose molecules. As a result, the loose NC fibers tend to adhere to each other upon drying strongly. This process is irreversible and dried NC material forms one solid and hard body that cannot be brought back into suspension. Prepared tablets of this composite (NC, MCC and active ingredient) gained noticeable hardness.

Hardness Dependency on NC Concentration.

Figure 3:
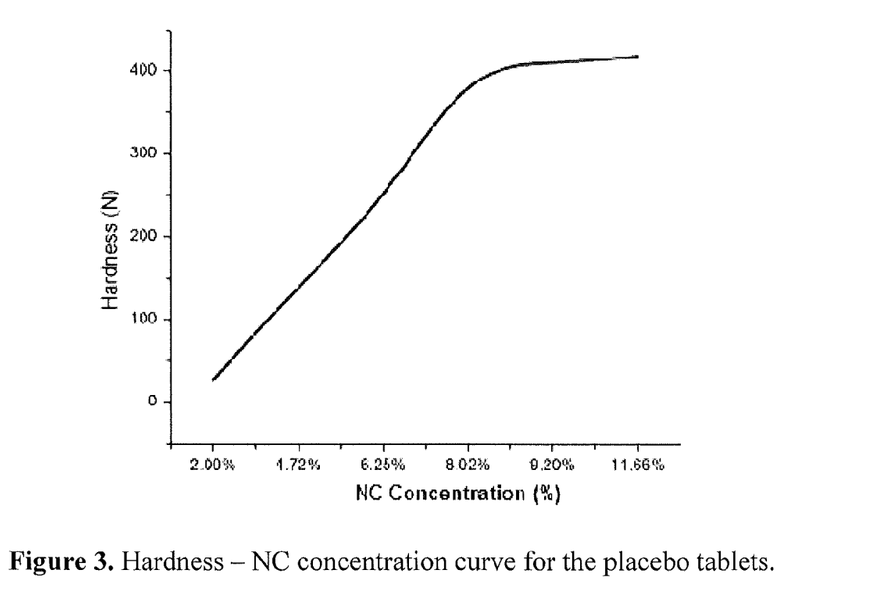
FIG. 3. Hardness—NC concentration curve for the placebo tablets. The hardness of the tablets was mainly controlled by NC concentration.

The dependency of tablet hardness on NC concentration was studied by measuring the hardness of placebo tablets prepared using different concentrations of NC. FIG. 3 shows the hardness—concentration curve for the prepared placebo tablets. It was noticed that the hardness of the placebo tablets increased over a wide range and up to 420N, which is a very high value for a cellulosic material. Also the hardness was mainly controlled by the concentration of NC. Tablets prepared by mixing MCC with water only disintegrated directly during the drying process. Also compressing MCC using TDP Single-Punch Tablet Press under a force of 6 kN was not enough to make hard tablets. Introducing NC to the tablet body is the reason behind the high hardness values. Increasing NC concentration increased the density of the cellulosic chains which allowed a more integrated network upon drying. Such characteristic makes the properties of the tablets, especially hardness, be easily controlled. It has to be mentioned that the curve exhibits a plateau at 420N only because of the maximum limit for the tablet tester equipment.

Slip-Casting.

The high hardness values, which can be achieved even using low NC concentrations, are the reason behind introducing MCC in the formula. MCC can dilute the tablets to enhance their size and weight; it also can decrease the hardness of the tablets to be suitable for customized drug delivery. MCC is already used as diluent in pharmaceuticals. Furthermore, it has lubricant and disintegrant properties that make it useful for tablets production. We found that mixing of MCC particles with the NC material is essential to reduce the shrinkage effects of NC upon drying. Also, the use of MCC is needed to reduce water absorption during storage that could be caused by the NC component.

Figure 4:
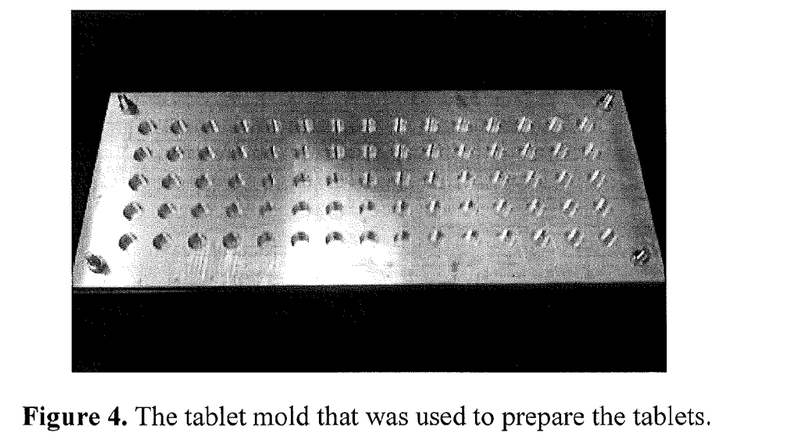
FIG. 4. The tablet mold that was used to prepare the tablets.

After slip-casted and while air-drying, the tablets showed shrinkage in volume that depended on the concentration of the used NC suspension (Table 3). Using the 11.66% NC suspension, the average diameter of the resultant tablets was 7.7 mm compared to 10.8 mm for the tablets produced using the 2.00% NC suspension. The hardness of the Paracetamol tablets showed an increase in the hardness values compared to the placebo tablets. The 2.00% Paracetamol tablets showed an average hardness of 58N, which is 31N higher that for the 2.00% placebo tablets. This change, due to the replacement of some of MCC by Paracetamol, can be explained by looking at the diameter difference between the two tablets formulas. Paracetamol tablet's diameter reduced to 9.6 mm compared to 10.8 mm for the placebo tablet. This reduction in diameter increased the density of fibers network and consequently increased the hardness of these Paracetamol tablets. FIG. 4 shows the tablet mold that was used to slip-cast the NC formulas and to fabricate the tablets.

TABLE 3

The variance in tablet shrinkage for different concentrations of NC.

| Placebo Tablets | | | Paracetamol Tablets | | |
|---|---|---|---|---|---|
| % NC | Diameter (mm) | % Shrinkage* | % NC | Diameter (mm) | % Shrinkage* |
| 2.00% | 10.8 | 10.0% | 2.00% | 9.6 | 20.0% |
| 4.72% | 9.4 | 21.7% | 3.00% | 8.9 | 25.8% |
| 6.25% | 9.0 | 25.0% | 4.00% | 8.3 | 30.8% |
| 8.02% | 8.5 | 29.2% | 5.00% | 8.1 | 32.5% |
| 11.66% | 7.7 | 35.8% | 6.00% | 7.8 | 35.0% |

*% Shrinkage = 100% − (Tablet Diameter/1.2 mm(Cast-Pore diameter)) * 100%.

Paracetamol Tablets Testing.

The testing results for the different Paracetamol tablets are enlisted in Table 4. The friability test was conducted on all the Paracetamol tablets. It reflects the hardness of the whole tablet body but mainly the outer hardness of tablet surface and edges. The weight loss percent was significantly less than 1%, which is the USP limit for this test. Mass variation and content uniformity are very important to evaluate the efficiency of the production technique and the homogeneity of the finished product. The very small relative standard deviation (RSD) values (<2.0%) of mass variation and content uniformity proved the high homogeneity of the tablets produced by slip-casting.

TABLE 4

Testing results of Paracetamol tablets using different NC concentrations.

| % NC | Friability Weight Loss (%) | Hardness Force (N) | Mass Variation RSD (%) | Content Uniformity RSD (%) | Drug Release Time (h) |
|---|---|---|---|---|---|
| 2% | 0.47% | 58 N | 1.5% | 0.56% | 5 Hours |
| 3% | 0.41% | 93 N | 0.8% | 0.82% | 13 Hours |
| 4% | 0.33% | 212 N | 0.9% | 1.0% | 20 Hours |
| 5% | 0.26% | 257 N | 1.2% | 0.73% | 24 Hours |
| 6% | 0.19% | 274 N | 1.0% | 1.3% | 24 Hours |

Figure 5:
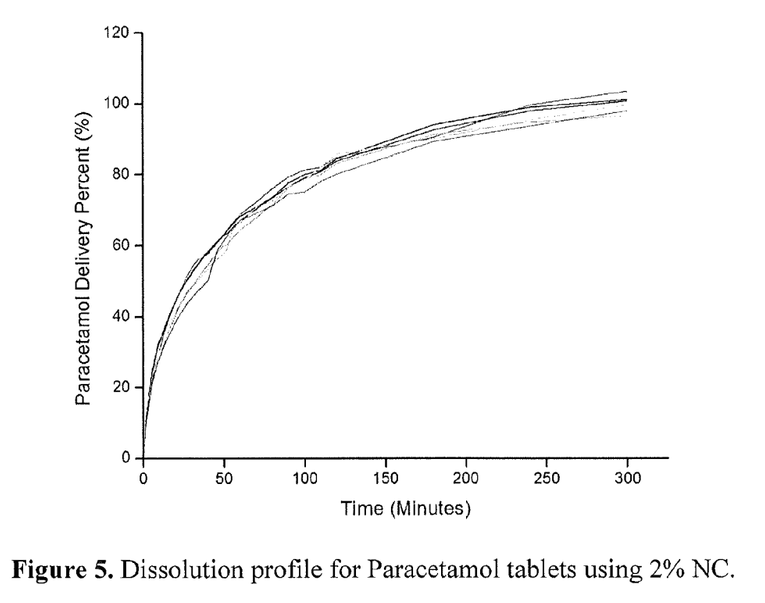
FIG. 5. Dissolution profile for Paracetamol tablets using 2% NC. Six tablets were tested at the same time. The identical release behavior of the tablets confirms the homogeneity of the tablet content.
Figure 6:
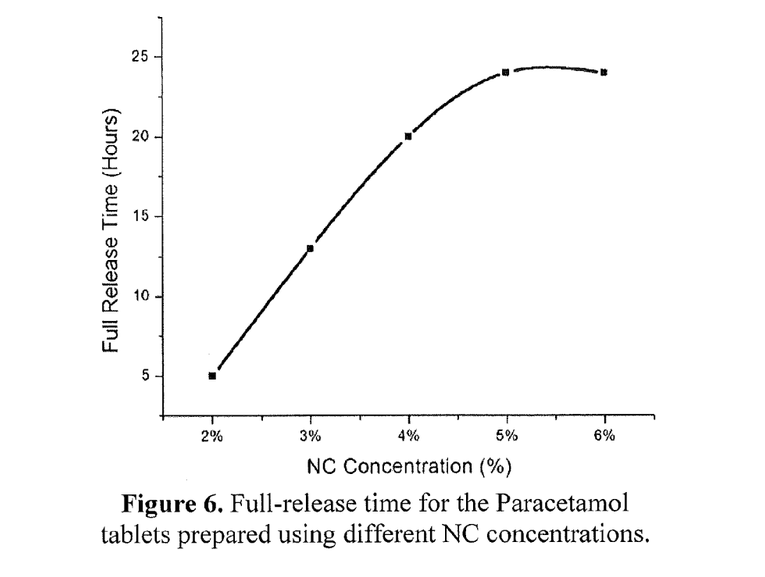
FIG. 6. Full-release time for the Paracetamol tablets prepared using different NC concentrations. The release rate was dependent on the NC concentration.

The drug release behavior for six tablets, prepared from each NC concentration, was studied. FIG. 5 shows the dissolution profile for the 30 mg Paracetamol tablets using 2% NC. Despite their hardness, Paracetamol tablets showed a full and gradual drug release and the release rate was very dependent on NC concentration (FIG. 6). The precision in release profiles (RSD=2.5%) is consistent with good content homogeneity of the finished product. FIG. 6 shows the effect of NC concentration on the release profile of the Paracetamol tablets. It clearly shows that we can tune the drug release profiles with NC concentration. The release behavior of these tablets starts with rapid release rate in the first 50 minutes and then released slower rate till complete release. This behavior is expected to minimize the fluctuation in the concentration of the drug molecules in the blood.

Tablets from Other Cellulose Sources and Using Ionic Liquids.

The NC material used previously was regenerated from MCC using sulfuric acid. It is interesting to investigate other sources of cellulose such as cotton cellulose and using alternative media to sulfuric acid such as ionic liquids. 2% NC suspensions were prepared by regeneration of MCC and CC using sulfuric acid and ionic liquids. The procedures of preparation were covered previously in chapter 3. The tablets were tested to study the effect of cellulose properties and the regeneration technique on its properties. Table 5 shows the results of testing these tablets.

TABLE 5

Testing results of Paracetamol tablets using 2% NC regenerated from different cellulose sources and using different solvents.[1]

| Cellulose Source | Solvent | Friability Weight Loss (%) | Hardness Force (N) | Drug Release Time (h) |
|---|---|---|---|---|
| MCC | Sulfuric Acid | 0.47% | 58 N | 5 Hours |
|  | Ionic Liquid | 0.35% | 67 N | 6 Hours |
| CC | Sulfuric Acid | 0.57% | 44 N | 3 Hours |
|  | Ionic Liquid | 0.54% | 53 N | 4 Hours |

[1]Degree of polymerization does not have a significant impact on tablet hardness. Tablet hardness controls the drug release.

Despite of the significant difference in the degree of polymerization of MCC and CC, there is only a slight difference in the behavior of the tablets prepared using their corresponding NC materials. The change in the full release time is mainly dependent on the hardness of the tablets. The data in Table 5 shows that there is a slight change in the tablet hardness when moving from sulfuric acid to ionic liquids. This difference might be due to the effect of these solvents on other NC properties such as crystallinity and sulfur content.

Conclusion.

The NC material showed a great ability to work as a multifunctional excipient to manufacture tablets with easily controlled properties. Tablets were prepared by slip-casting of simple formulas of NC and cellulose, with Paracetamol as the active ingredient. The prepared tablets showed interesting controlled hardness and drug delivery properties, which were mainly dependent on NC concentration. This characteristic helps reducing the time energy, and materials required to optimize the properties of drug formulas. The gel nature of the material improved the homogeneity of the drug formula and consequently the content uniformity of the tablets. The precise content and mass uniformity values proved the efficiency of slip casting as a technique to fabricate tablets. The simple manufacturing process opened the door to implement continuous processing in tablet production.

The foregoing is illustrative of the present invention, and is not to be construed as limiting thereof. The invention is defined by the following claims, with equivalents of the claims to be included therein.

That which is claimed is:

1. A method of making a pharmaceutical tablet, comprising:
 (a) producing an aqueous networked cellulose gel by: (i) hydrolyzing cellulose in an acidic dissolution media at a temperature of 5 to 40° C. for 10 to 60 minutes to form a first mixture; (ii) precipitating said hydrolyzed cellulose by combining said first mixture with an antisolvent, and then, in any order; (iii) separating said cellulose precipitate from said antisolvent and acidic dissolution media; (iv) adjusting or neutralizing the pH of said cellulose precipitate to a pH of from 4 to 9; and (v) washing said cellulose precipitate with water to form said aqueous networked cellulose gel;
 (b) combining (i) said aqueous networked cellulose gel with (ii) water insoluble particulate filler and (iii) a water soluble active agent to form a mixture thereof;
 (c) casting said mixture to form a wet tablet;
 (d) drying said wet tablet to form a dry pharmaceutical tablet; and then
 (e) optionally coating said tablet.

2. The method of claim 1, wherein said water insoluble filler comprises microcrystalline cellulose.

3. The method of claim 1, wherein said dry pharmaceutical tablet does not fracture under a force of 50 Newtons as applied by a tablet press.

4. The method of claim 1, wherein said pharmaceutical tablet shrinks less than 40 percent in diameter during said drying step.

5. The method of claim 1, wherein said casting step is carried out at atmospheric pressure.

6. The method of claim 1, wherein said drying step is carried out by air drying at room temperature, by heating, by vacuum drying, or a combination thereof.

7. The method of claim 1, wherein said active agent is selected from the group consisting of paracetamol, aspirin, ibuprofen, naproxen, Atorvastatin, Clopidogrel, Esomeprazole, Amlodipine, Olanzapine, Valsartan, Risperidone, Venlafaxine, Pantoprazole, Montelukast, Quetiapine, Rosiglitazone, Pioglitazone, Simvastatin, Escitalopram, Donepezil, Irbesartan, Rosuvastatin, Aripiprazole, Candesartan, Sildenafil, Levofloxacin, Duloxetine, Methylphenidate, and pharmaceutically acceptable salts thereof.

8. The method of claim 1, said dry pharmaceutical tablet comprising:
    (a) from 2 to 80 percent by weight of networked cellulose;
    (b) from 10 to 95 percent by weight of filler;
    (c) from 0.1 to 20 percent by weight of an active agent; and
    (d) optionally, from 0.05 to 10 percent by weight of an enteric coating.

9. A pharmaceutical tablet produced by the process of claim 1.

10. The pharmaceutical table of claim 9, comprising:
    (a) from 2 to 80 percent by weight of networked cellulose;
    (b) from 10 to 95 percent by weight of filler;
    (c) from 0.1 to 20 percent by weight of an active agent; and
    (d) optionally, from 0.05 to 10 percent by weight of a coating.

11. The tablet of claim 10, wherein said water insoluble filler comprises microcrystalline cellulose.

12. The tablet of claim 10, wherein said dry pharmaceutical tablet does not fracture under a force of 50 Newtons.

13. The tablet of claim 10, wherein said tablet does not fracture under a force of 150 Newtons.

14. The tablet of claim 10, wherein said active agent is selected from the group consisting of paracetamol, aspirin, ibuprofen, naproxen, Atorvastatin, Clopidogrel, Esomeprazole, Amlodipine, Olanzapine, Valsartan, Risperidone, Venlafaxine, Pantoprazole, Montelukast, Quetiapine, Rosiglitazone, Pioglitazone, Simvastatin, Escitalopram, Donepezil, Irbesartan, Rosuvastatin, Aripiprazole, Candesartan, Sildenafil, Levofloxacin, Duloxetine, Methylphenidate, and pharmaceutically acceptable salts thereof.

15. The tablet of claim 10, wherein said active agent is included in an amount of from 0.01 to 4000 milligrams per tablet.

16. A pharmaceutical tablet of claim 10 consisting essentially of:
    (a) from 2 to 80 percent by weight of networked cellulose;
    (b) from 10 to 95 percent by weight of filler;
    (c) from 0.1 to 20 percent by weight of an active agent selected from the group consisting of paracetamol, aspirin, ibuprofen, naproxen, Atorvastatin, Clopidogrel, Esomeprazole, Amlodipine, Olanzapine, Valsartan, Risperidone, Venlafaxine, Pantoprazole, Montelukast, Quetiapine, Rosiglitazone, Pioglitazone, Simvastatin, Escitalopram, Donepezil, Irbesartan, Rosuvastatin, Aripiprazole, Candesartan, Sildenafil, Levofloxacin, Duloxetine, Methylphenidate, and pharmaceutically acceptable salts thereof; and
    (d) optionally, from 0.05 to 10 percent by weight of a coating;
    wherein said tablet does not fracture under a force of 50 Newtons.

17. The tablet of claim 16, wherein said water insoluble filler comprises microcrystalline cellulose.

18. The method of claim 1, wherein:
    said dry pharmaceutical tablet does not fracture under a force of 50 Newtons as applied by a tablet press; and
    said pharmaceutical tablet shrinks less than 40 percent in diameter during said drying step.

19. The method of claim 1, wherein said antisolvent is ethanol or water.

20. The method of claim 1, wherein:
    said dry pharmaceutical tablet does not fracture under a force of 50 Newtons as applied by a tablet press;
    said pharmaceutical tablet shrinks less than 40 percent in diameter during said drying step;
    said casting step is carried out at atmospheric pressure;
    said drying step is carried out by air drying at room temperature, by heating, by vacuum drying, or a combination thereof;
    said active agent is selected from the group consisting of paracetamol, aspirin, ibuprofen, naproxen, Atorvastatin, Clopidogrel, Esomeprazole, Amlodipine, Olanzapine, Valsartan, Risperidone, Venlafaxine, Pantoprazole, Montelukast, Quetiapine, Rosiglitazone, Pioglitazone, Simvastatin, Escitalopram, Donepezil, Irbesartan, Rosuvastatin, Aripiprazole, Candesartan, Sildenafil, Levofloxacin, Duloxetine, Methylphenidate, and pharmaceutically acceptable salts thereof;
    said dry pharmaceutical tablet comprising: (a) from 2 to 80 percent by weight of networked cellulose; (b) from 10 to 95 percent by weight of filler; (c) from 0.1 to 20 percent by weight of an active agent; and (d) optionally, from 0.05 to 10 percent by weight of an enteric coating.

21. The method of claim 20, wherein said active agent is paracetamol.

22. A pharmaceutical tablet of claim 16, wherein said active agent is paracetamol.

* * * * *